United States Patent [19]

Gosciniak

[11] Patent Number: 4,848,570
[45] Date of Patent: Jul. 18, 1989

[54] SHARPS DISPOSAL SYSTEM

[75] Inventor: John Gosciniak, LaPorte, Ind.

[73] Assignee: Multimedia Marketing, Inc., Roselle, Ill.

[21] Appl. No.: 209,835

[22] Filed: Jun. 22, 1988

[51] Int. Cl.$^4$ .............................................. A61M 5/32
[52] U.S. Cl. .................................. 206/366; 220/350; 220/20.5; 232/43.2
[58] Field of Search .................... 220/1 T, 20.5, 22.5, 220/350, 253; 206/366, 370, 63.5; 232/43.2, 43.5

[56] References Cited

U.S. PATENT DOCUMENTS

| | | | |
|---|---|---|---|
| 4,162,024 | 7/1979 | Shanley | 220/350 |
| 4,375,849 | 3/1983 | Hanifl | 206/366 |
| 4,465,187 | 8/1984 | Kinard | 220/350 |
| 4,485,918 | 12/1984 | Mayer | 206/366 |
| 4,576,281 | 3/1986 | Kirksey | 206/370 |
| 4,662,516 | 5/1987 | Baker | 206/366 |
| 4,715,498 | 12/1987 | Hanifl | 206/366 |

*Primary Examiner*—Stephen Marcus
*Assistant Examiner*—Gilbert W. Reece
*Attorney, Agent, or Firm*—Welsh & Katz, Ltd.

[57] ABSTRACT

A sharps disposal system includes a holding chamber and a collecting chamber. The open bottom of the holding chamber is closed off by a bottom cover plate as sharps are accumulated. The bottom cover plate is confined by a locked articulated safety door which prevents accidental premature opening of the bottom of the holding chamber. When the accumulated sharps are to be removed from the holding chamber, the articulated safety door is unlocked and slid in a track from the bottom of holding chamber to the front wall. The collecting chamber is then inserted into the bottom of the holding chamber. The open top of the collecting chamber has a track holding a top cover plate. The top cover plate interlocks with the holding chamber bottom cover plate, and the two cover plates are withdrawn as a unit to allow the accumulated sharps to drop into the collecting chamber. The two cover plates are returned to the closed position and the interlock is disengaged to allow the collecting chamber to be withdrawn from the bottom of the holding chamber. The articulated safety door is returned to the closed position and locked to confine the bottom cover plate of the holding chamber.

36 Claims, 3 Drawing Sheets

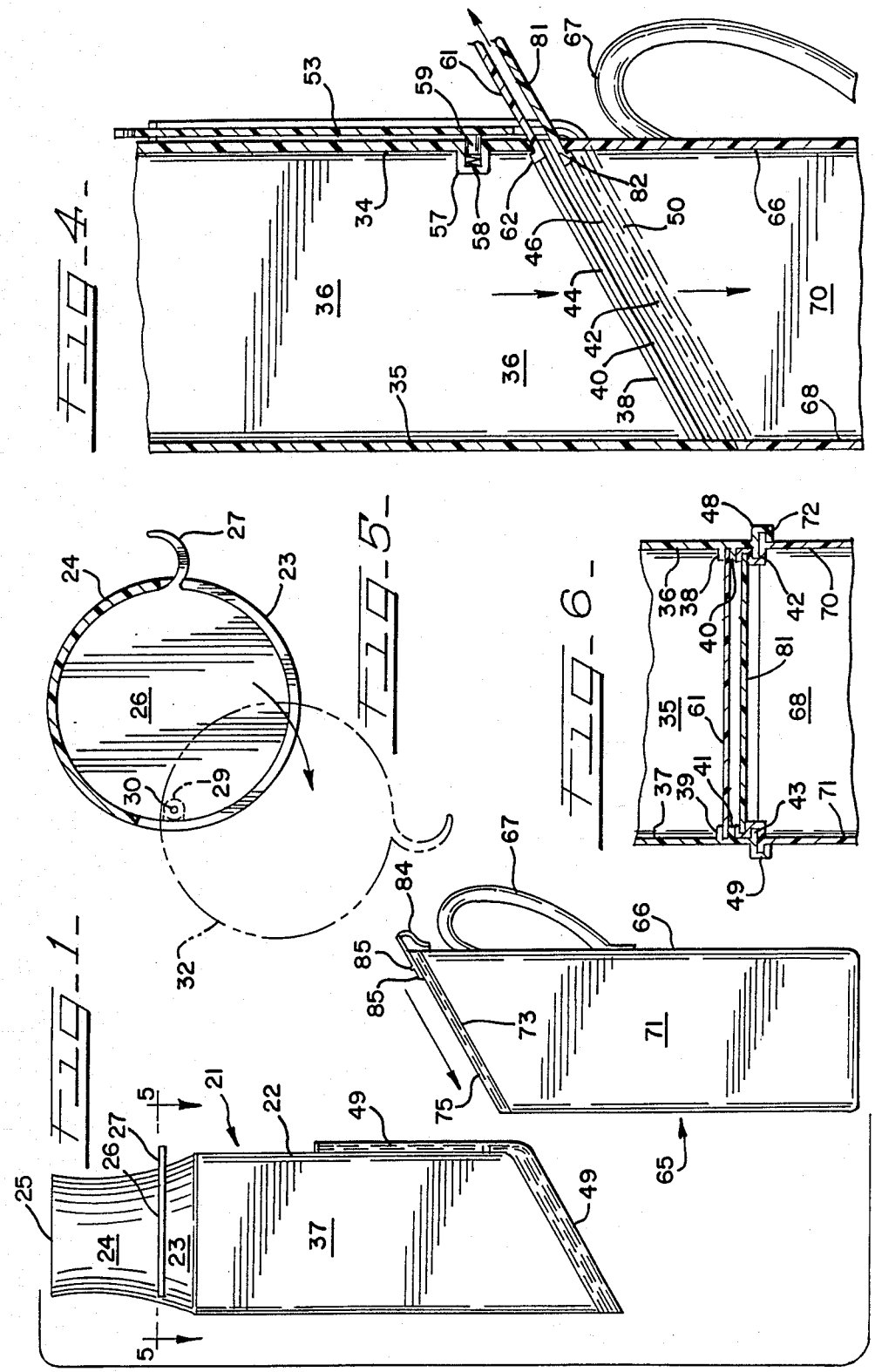

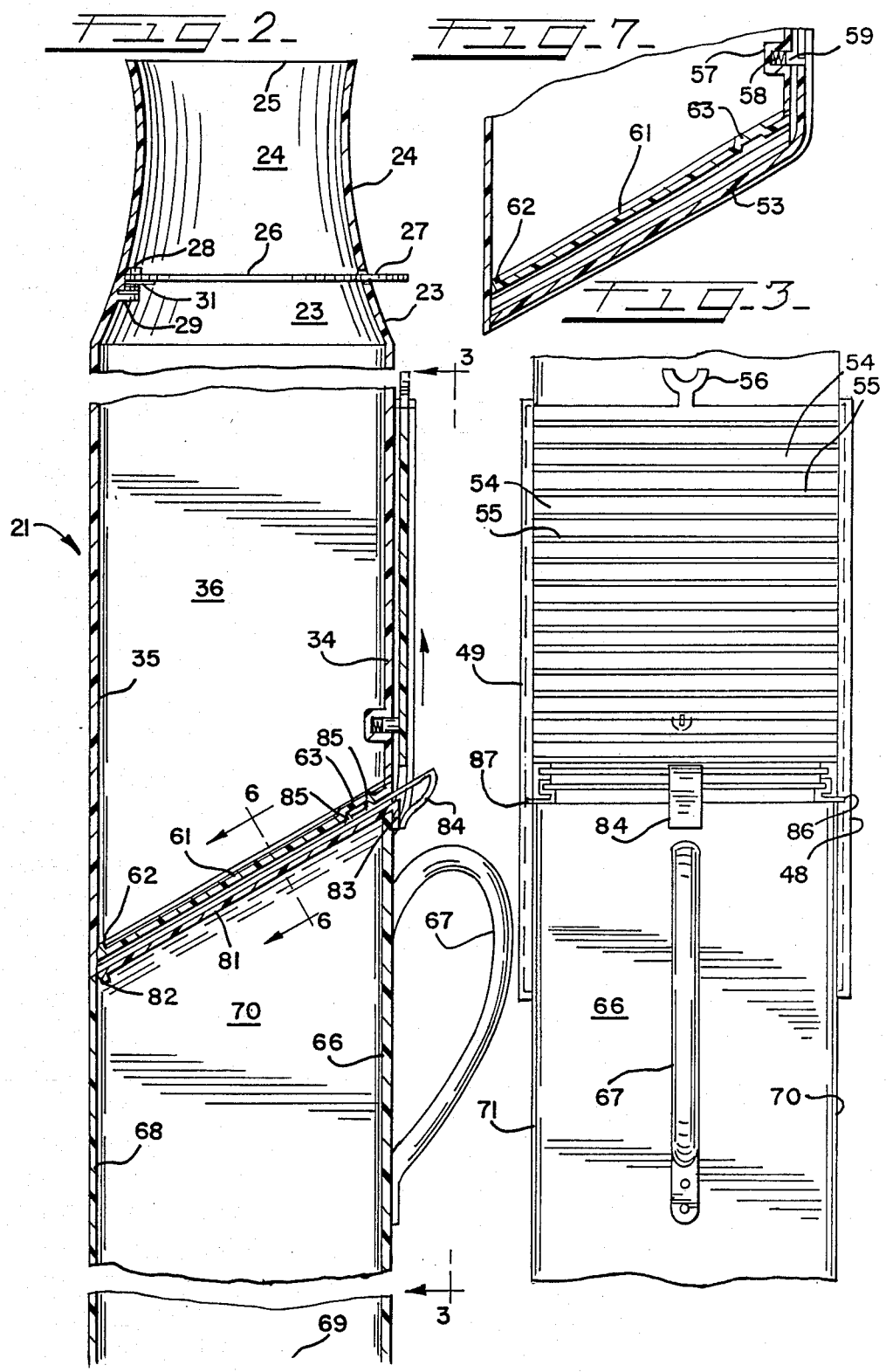

SHARPS DISPOSAL SYSTEM

BACKGROUND OF THE INVENTION

The present invention relates to the disposal of contaminated and hazardous items, and in particular, to the disposal of sharps in a hospital or similar medical environment.

The term "sharps" is defined as articles having a sharp point or a sharp cutting edge. In a hospital environment, sharps are generally hypodermic injection syringe needles, single use disposable syringes with the needles attached, and single or double-ended sampling needles which are thread engaged to a sampling syringe body. After use, the tip of a hypodermic needle may bear a variety of diseases, such as hepatitis or AIDS (Acquired Immune Deficiency Syndrome), which can be communicated to one who is accidentally pricked or stuck by the used needle. So prevalent are such accidental needle sticks that some estimates suggest that millions of dollars a year are spent in running blood tests following needle sticks to discover whether or not a disease may have been communicated, and to prophylactically treat the potential disease when such tests are positive. This cost is reflected in increased medical bills which are paid by all users of the hospital facility. Because of this problem, current guidelines of the U.S. Center for Disease Control require immediate disposal of hypodermic needles or other sharps at their site of use immediately following an injection.

Accordingly, it is an object of the present invention to provide a novel sharps disposal system.

It is another object of the present invention to provide a sharps disposal system which is secure in that it cannot be accidentally opened or easily intentionally invaded.

These and other objects of the present invention, as well as the advantages thereof, will become clear from the disclosure which follows.

SUMMARY OF THE INVENTION

The foregoing objects may be achieved by a sharps disposal system using two different container devices. The first device is a holding chamber and the second device is a collecting chamber which is utilized to withdraw the discarded sharps when the holding chamber has become full.

In one preferred embodiment, the present invention comprehends a container apparatus, suitable for use in a sharps disposal system, which comprises in combination:

a. a holding chamber, including a holding chamber body member having a rectangular cross section with an open top and an open bottom, having front and back walls, and having right and left side walls;

b. inwardly facing elongated first grooves on the inside of the right and left side walls, proximate the bottom of the holding chamber body member, and running from the back wall to the front wall;

c. inwardly facing elongated second grooves on the inside of the right and left side walls, proximate the bottom of the holding chamber body member, positioned below the first grooves, and running from the back wall to the front wall;

d. outwardly extending ribs located below and on the outside of the bottom edge of the right and left side walls, the ribs containing inwardly facing elongated third grooves proximate the bottom of the holding chamber body member and positioned below and outside of the first and second grooves, the ribs running from the back wall and extending upwardly along the corners formed by the holding chamber front wall with the side walls and continuing the inwardly facing third grooves vertically along the corners;

e. a holding chamber bottom cover plate, slidably positioned in the first grooves to provide means to close the open bottom of the holding chamber body member, and to open the bottom by being withdrawn along the first grooves and under the holding chamber body member front wall; and, f. a flexible safety door, slidably positioned in the third grooves and movable from a closed to an open position, the flexible safety door in closed position enclosing the bottom cover plate below the holding chamber bottom and along the bottom of the holding chamber front wall to prevent the withdrawal of the bottom cover plate along the first grooves, and the flexible safety door in open position being slidably movable within the third grooves from below the holding chamber bottom to a position along the outer surface of said holding chamber body member front wall above the first and second grooves, whereby the bottom cover plate may be withdrawn to open the holding chamber bottom.

The container system of the present invention may be further characterized in that the holding chamber includes a neck on top of the chamber body member and the neck has an upper portion and a lower portion with a closure plate movably positioned therebetween. The closure plate is movable from a closed to an open position, thereby to allow sharps to be dropped into the holding chamber. In one preferred embodiment the closure plate is pivotably mounted in the neck with a biasing means retaining the closure plate in a closed position until external force is applied to pivot the closure plate to an open position, whereupon the biasing means returns the closure plate to the closed position when the external force is removed.

The holding chamber further includes a locking means on the front wall of the holding chamber body member, coacting with means on the flexible safety door to retain the safety door in closed position enclosing the bottom cover plate, thereby preventing inadvertent premature opening of the safety door and withdrawal of the bottom cover plate to prematurely open the bottom of the holding chamber. This eliminates the danger that the accumulated sharps may be inadvertently dropped from the holding chamber to the floor or onto a table top, thereby causing a potential sticking hazard.

The present invention further comprehends a collecting chamber having a rectangular cross-section substantially congruent with the cross section of the holding chamber body member, having an open top and a closed bottom, having front and back walls, having right and left side walls, and further including inwardly extending ribs located above and on the inside of the top edge of the left and right collecting chamber side walls, the ribs running from the collecting chamber back wall to the collecting chamber front wall, the ribs containing inwardly facing elongated fourth grooves, and the ribs having outside dimensions enabling the ribs to slidably fit within the second grooves of the holding chamber body member.

The collecting chamber also includes a top cover plate which is slidably positioned in the fourth grooves to provide means to close the open top of the collecting chamber and to open the top by being withdrawn along the fourth grooves and over the collecting chamber front wall. The container system is further characterized in that the holding chamber bottom cover plate has a first detent element on its bottom surface and the collecting chamber top plate has a second detente element on its top surface, so that the first and second detent elements are dimensioned and positioned to releasably interlock the two cover plates together when the collecting chamber is slid into the second grooves in the holding chamber, whereby said cover plates may be withdrawn in the first and fourth grooves respectively as an interlocked unit to allow the accumulated sharps in the holding chamber to drop into the collecting chamber.

A clearer understanding of the present invention will be obtained from the disclosure which follows when read in light of the accompanying drawings.

BRIEF DESCRIPTION OF THE DRAWINGS

FIG. 1 is a left side elevational view of the sharps container system of this invention showing the collecting chamber positioned for insertion into the bottom grooves of the holding chamber.

FIG. 2 is a left side elevational view of the sharps container system of FIG. 1, shown as a cross-sectional view, with the collecting chamber inserted into the bottom grooves of the holding chamber.

FIG. 3 is a front elevational view of the sharps container system of FIG. 1 with the collecting chamber inserted into the bottom grooves of the holding chamber.

FIG. 4 is a left side elevational view of the sharps container system of FIG. 1, shown as a cross-sectional view with the collecting chamber inserted into the grooves of the holding chamber, and showing the bottom cover plate and the top cover plate in a withdrawn position.

FIG. 5 is a cross-sectional view of FIG. 1 taken along the section line 5—5.

FIG. 6 is a cross-sectional view of FIG. 2 taken along the section line 6—6.

FIG. 7 is a left side elevational view of the bottom portion of the holding chamber of FIG. 1, shown in cross-section, illustrating the bottom cover plate and the flexible safety door in closed position.

DESCRIPTION OF THE PREFERRED EMBODIMENT

Figure 8:
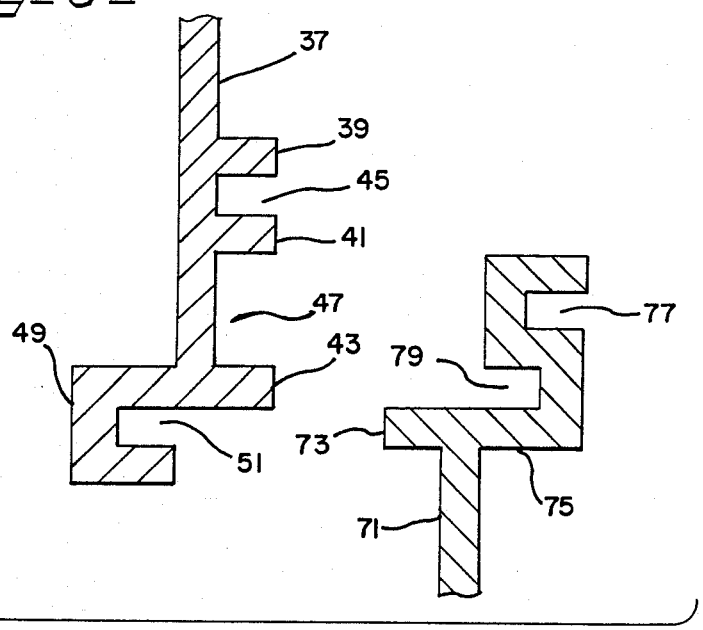
FIG. 8 is a simplified schematic representation of the bottom portion of the left side wall of the holding chamber and the mating top portion of the left side wall of the collecting chamber.

Referring now to FIG. 1 there is shown a holding chamber 21 and a collecting chamber 65. Collecting chamber 65 is shown separated from the holding chamber 21 and ready for insertion into the bottom of holding chamber 21 as indicated by the directional arrow. Holding chamber 21 is typically supported upon a vertical support, such as a column or a wall, by supporting attachment means which is not shown.

Holding chamber 21 comprises a holding chamber body member 22 having a substantially rectangular cross-section. The holding chamber body member has an open top and an open bottom. At the upper end of the holding chamber there is a necked down section. This neck consists of a lower portion 23 which provides a transition from a rectangular cross section to a circular cross - section, and an upper portion 24 which has a circular cross section. At the top of the neck upper portion 24 there is a circular open mouth 25. Between the neck lower and upper portions 23 and 24 there is a circular closure plate 26.

The circular closure plate is interposed between the upper and lower neck portions as a means of keeping the open top in a normally closed position when sharps are not being inserted into the holding chamber. As seen most clearly in FIG. 5, the circular closure plate 26 has a finger gripping tab 27 by means of which the closure plate may be pivoted out of position to open the neck of the holding chamber. This open position is shown by the phantom line 32. The circular closure plate 26 is supported within the neck of the holding chamber by upper and lower lugs 28 and 29 which are shown most clearly in FIG. 2. A pin 30 passes between the lugs and through the circular closure plate 26 to provide a means of pivoting the closure plate in and out of the neck. A spring 31 is also mounted between the lugs 28 and 29 and on the pin 30. Spring 31 is attached to the circular closure plate in order to bias the closure plate into a closed position. When finger pressure is exerted onto the finger grip 27, the closure plate will pivot into the open position shown by the phantom line 32, and the spring 31 will return the closure plate to the closed position when the finger pressure is removed from the finger grip 27. Safety is assured by keeping the closure plate biased in a closed position, since a person cannot accidentally place a hand or finger into the holding chamber and thereby accidentally injure himself.

The holding chamber body member 22 has a front chamber wall 34 and a back wall 35, as seen most clearly in FIG. 2. The holding chamber body member also has a right side wall 36 and a left side wall 37. As seen most clearly in FIG. 1 the side walls of the holding chamber body member have the shape of a trapezoid. The bottom edge of the side walls 36 and 37 is slanted downwardly from the front wall to the back wall of the holding chamber body member. This slant is preferably about 30 degrees from the horizontal.

When the holding chamber is being used to accumulate disposed of sharps, the open bottom is closed off by a bottom cover plate 61 which can be seen most clearly in FIG. 2. The bottom cover plate is held within elongated upper grooves or tracks which run parallel to and along the full length of the sloping bottom edges of the side walls 36 and 37. In order to provide that the bottom cover plate 61 may not be accidentally removed from the bottom of the holding chamber 21, a safety door is provided. The safety door is similarly positioned in a pair of bottom grooves or tracks below the bottom cover plate 61. This safety door encloses the entire bottom of the bottom cover plate as well as the front of the bottom cover plate so that the cover plate may not be withdrawn when the safety door is in closed position. The safety door is capable of flexing about axes normal to its direction of travel substantially throughout its length. A preferred safety door 53 is shown most clearly in FIG. 3 as being articulated. Other flexible safety doors, such as those of a flexible plastic planar structure, may also be used. Articulated safety door 53 is made up of a plurality of individual panels 54 which are hinged together by hinge elements 55 located between pairs of panels.

A locking yoke and handle 56 is provided for pulling the safety door into an open position. The yoke 56 is located at the top of the safety door, as shown in FIG. 3. This locking yoke interacts with a spring biased lock 59, which is located on the front wall of the holding chamber body member, to hold the safety door in closed position, as shown in FIG. 7. The spring biased lock is contained in a recess 57 in the body member front wall 34. A spring 58 is located in recess 57 and it biases the lock 59 into an outward projecting position, whereby the lock can interact with the locking yoke 56 so that the safety door may not be opened unless an authorized person intentionally unlocks the lock and opens the door. This is done by inserting a key into the lock to unlock it, and then pushing the projecting lock down into the recess 57. The yoke 56 is grasped with the fingers of the other hand and pulled upwardly to pull the safety door along the bottom tracks and up an extension of the tracks along the outer surface of the front wall 34, to the position shown in FIGS. 3 and 4.

When the safety door has been pulled up into the open position, the collecting chamber 65 may be inserted into the bottom of the holding chamber 21 along the pair of bottom grooves or tracks which has been vacated by the articulated safety door. The collecting chamber is simultaneously inserted along a pair of central grooves or tracks located between the upper and lower tracks. (The tracks will be more fully discussed hereinafter.) When this insertion has occurred, the sharps disposal system assumes the configuration which is shown in FIGS. 2 and 4.

The collecting chamber 65 has a rectangular configuration which is substantially congruent to the rectangular configuration of the holding chamber body member 22. The collecting chamber has a front wall 66 on which is mounted a gripping handle 67 which provides means for easily inserting and withdrawing the collecting chamber from the holding chamber 21. The collecting chamber also has a back wall 68 and a closed bottom 69. Additionally, the collecting chamber is provided with a right side wall 70 and a left side wall 71. These side walls also have the shape of a trapezoid. The top portion of the collecting chamber side walls is slanted downwardly from the front wall 66 towards the back wall 68. This slant is also preferably at an angle of about 30 degrees from the horizontal so that the collecting chamber 65 will easily mate with the bottom of the holding chamber 21 and yet not allow the sharps to be inadvertently exposed and dropped when transferring from the holding chamber to the collecting chamber. The top of the collecting chamber 65 is normally closed by a top cover plate 81. Top cover plate 81 is held along the top edge of the collecting chamber 65 in a pair of tracks or grooves which run parallel to and along the full length of the sloping top of the collecting chamber side walls.

Figure 9:
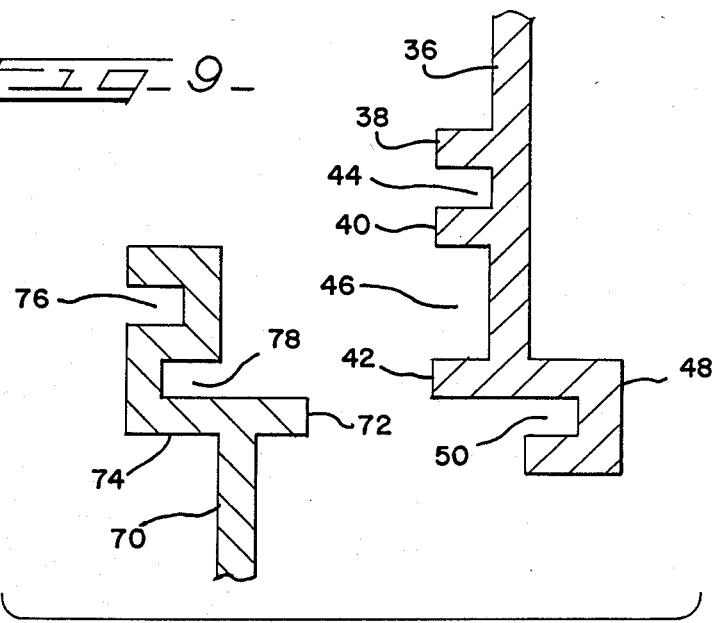
FIG. 9 is a simplified schematic representation of the bottom portion of the right side wall of the holding chamber and the mating top portion of the right side wall of the collecting chamber.

The elongated grooves which run along the bottom edges of the side walls 36 and 37 of the holding chamber 21 nd the elongated grooves which run along the top of the collecting chamber side walls 70 and 71 are illustrated most clearly in FIGS. 8 and 9.

Referring now to FIG. 8, there is shown the lower portion of the holding chamber left side wall 37. The bottom of the holding chamber left side wall has an upper internal projection or rib 39, a center internal projection or rib 41 and a lower projection or rib 43. These elongated ribs or projections define a pair of grooves in the left side wall. An upper groove or track 45 is found between the ribs 39 and 41, and a center groove or track 47 is found between the ribs 41 and 43. The bottom edge of the left side wall 37 has a bottom outer rib 49 which has a C-shape. The elongated outer rib 49 defines a bottom groove 51 which is contained within the C-shaped outer rib.

Also seen in FIG. 8 is the top portion of the left side wall 71 of the collecting chamber. This top portion has an outer rib 73 on the outside of the left side wall. It also has an inner upstanding S-shaped rib or projection 75. The S-shaped rib or projection 75 defines an upper inner groove 77 and an outer lower groove 79.

It can be seen from FIG. 8 that the lower groove 79 in the S-shaped rib of the collecting chamber will mate with the lower rib 43 in the bottom of the left side wall 37 of the holding chamber. Similarly, the upper portion of the S-shaped rib 75 of the collecting chamber will mate in the central groove 47 in the bottom of the side wall 37 of the holding chamber. Additionally, the outer rib 73 at the top of the side wall 71 of the collecting chamber will mate in the bottom groove 51 of the holding chamber. These mating portions allow the collecting chamber 65 to be slidably inserted into the bottom of the holding chamber 21 when the safety door has been opened.

FIG. 9 illustrates the right side wall 36 of the holding chamber and the right side wall 70 of the collecting chamber. The right side wall 36 of the holding chamber 21 has an upper internal projection or rib 38, a center internal projection or rib 40, and a lower projection or rib 42. These elongated inner projections or ribs define an upper groove or track 44 in the right side wall located between ribs 38 and 40, and a center groove or track 46 located between the ribs 40 and 42. In addition, the bottom edge of the right side wall 36 has an elongated bottom outer rib having a reversed C-shape. As used herein, the term "C-shape" includes a standard C-shape and a reversed C-shape. The reversed C-shaped rib 48 has a bottom internal groove or track 50 within its structure.

Also seen in FIG. 9 is the upper portion of the right side wall 70 of the collecting chamber. At the upper edge of the side wall 70 there is an elongated outer rib 72. There is also an elongated inner upstanding S-shaped projection 74 which is a reversed S-shape. As used herein, the term "S-shape" includes a standard S-shape and a reversed S-shape. The upstanding S-shaped rib 74 defines an inner groove or track 76 and an outer groove or track 78.

It will be seen that the upper end of the right side wall 70 of the collecting chamber will mate with the lower grooves in the bottom edge of the right side wall of the holding chamber. The rib 72 of the collecting chamber will mate with the groove 50 of the holding chamber. The rib 42 of the holding chamber will mate with the groove 78 of the collecting chamber. In addition, the upper portion of the S-shaped rib 74 of the collecting chamber will mate in the groove 46 of the holding chamber.

The collecting chamber top cover plate 81 is slidable within the inner groove or track 77 of the left side wall 71 and the inner groove or track 76 of the right side wall 70 of the collecting chamber. In addition, the bottom cover plate 61 of the holding chamber is slidable within the groove 44 of the right side wall of the holding chamber and the groove 45 in the left side wall of the holding chamber. Grooves 44 and 45 are positioned sufficiently close to grooves 76 and 77 so that top cover plate 81 is closely adjacent to bottom cover plate 61 yet not so close as to interfere with the opening and closing movement. Thus, no blood or other fluid can splash between the plates 61 and 81 during the transfer operation, which could cause contamination of the entire unit.

The interlocking elements which are shown separated in FIGS. 8 and 9 are shown in the interlocked position in FIG. 6. Referring now to FIG. 6, there is also shown the bottom cover plate 61 positioned in the upper tracks 44 and 45 of the holding chamber side walls, and the top cover plate 81 positioned in the tracks or grooves 76 and 77 in the top of the side walls of the collecting chamber. FIG. 6 also clearly shows how the various ribs and grooves mate and interlock between the holding chamber 21 and the collecting chamber 65.

As previously noted hereinabove, the articulated safety door 53 encloses the bottom cover plate 61 so that it cannot be inadvertently withdrawn along the upper tracks 44 and 45 when the collection chamber 65 is not attached to the holding chamber 21. The safety door is slidable within the bottom grooves or tracks 50 and 51 of the holding chamber. The C-shaped outer ribs 48 and 49 which contain the bottom tracks 50 and 51 run along the sloped bottom edges of the side walls 36 and 37 from the back wall 35 to the front wall 34. The C-shaped outer ribs then curve upwardly at the front wall 34 and continue on the outside of the side walls along the corners formed by the holding chamber front wall and the side walls. The bottom grooves or tracks 50 and 51 thus also curve upwardly and run vertically along the corners to enable the articulated safety door to be pulled upwardly along the outer surface of the front wall when it is desired to attached the collecting chamber to the holding chamber for the removal of accumulated sharps. This change in direction of the ribs 48 and 49 from the bottom slope to the vertical rise is seen most clearly in FIGS. 2, 3 and 4.

When the articulated safety door has been removed from the bottom of the holding chamber, the collecting chamber is united with the bottom of the holding chamber. This is shown in FIG. 6. The upper portions of the S-shaped upstanding projections or ribs 74 and 75 on the collecting chamber side walls are mated with the central grooves or tracks 46 and 47 on the holding chamber side walls. Additionally, the outer projections or ribs 72 and 73 of the collecting chamber are mated with the bottom grooves or tracks 50 and 51 on the bottom of the holding chamber, this bottom portion of tracks 50 and 51 having been vacated by the safety door. Outer ribs 72 and 73 slide into the grooves 50 and 51 by means of notches 86 and 87 which are shown in FIG. 3. These notches do not interfere with the action of the articulated safety door because the top edge of the safety door is always above the location of the notches whether the safety door is in open position or in closed position.

A method of using the sharps disposal system of the present invention will now be described. When the holding chamber 21 is ready to discharge accumulated sharps, the bottom cover plate 61 will be in position to close off the open bottom of the holding chamber. In addition, the articulated safety door will be in the closed position, as illustrated in FIG. 7. Spring biased lock 59 will be projecting from the face of the front wall of the holding chamber, thereby interacting with the yoke 56 on the articulated safety door to keep the safety door in the closed position. When the sharps have been accumulated to the point where they must be removed from the holding chamber, the attendant who is responsible for the removal will take a key to unlock the spring biased lock 59 and depress it into the recess 57, thereby enabling the articulated safety door 53 to be slid upwardly in its tracks and into position on the front face of the holding chamber front wall 34. This condition is illustrated in FIGS. 2 and 3.

At this point the collecting chamber 65, which contains the top cover plate 81 in position closing off the open top of the chamber, will now be inserted into the bottom of the holding chamber 21. This condition is shown in FIGS. 2 and 3. It will be seen in FIG. 2 that the top cover plate 81 of the collecting chamber 65 and the bottom cover plate 61 of the holding chamber 21 are both located in the closed position. The top cover plate 81 of the collecting chamber has a depending lip 83. Attached to the depending lip 83 is a ribbon spring trigger or handle 84. This ribbon spring handle contains at least one and preferably two detent teeth 85 on the inner end of the spring trigger or handle 84. These teeth interact with a detent recess 63 which is located in the bottom surface of the holding chamber bottom cover plate 61. Detent recess 63 holds the teeth 85 of the trigger 84 so that the two cover plates can now be removed as a unit. The person collecting the accumulated sharps grips the trigger or handle 84 and withdraws both the bottom cover plate 61 and the top cover plate 81 along their respective tracks to an open position which is shown in FIG. 4. This allows the accumulated sharps to drop out of the holding chamber 21 and into the receiving chamber 65.

It will be seen in FIGS. 2 and 4 that the bottom cover plate 61 has an upstanding rear rib 62 and the top cover plate 81 has an depending rear rib 82. These two rear ribs 62 and 82 run across the entire width of the bottom cover plate 61 and the top cover plate 81 respectively, and prevent them from being completely withdrawn from the grooves or tracks in which they are sliding. It will be noted that the upstanding rear rib 62 on bottom cover plate 61 is substantially perpendicular to the plane of the cover plate 61, and that depending rib 82 is substantially perpendicular to top cover plate 81. Those skilled in the art will recognize that these retaining elements need not be perpendicular, although that is preferred, and that they can extend at an oblique angle. Additionally, they can protect upwardly or downwardly. Alternatively, the retaining elements can be in the same plane as the cover plate, such as a pair of ears or lugs extending from the side edges at the back of the cover plate, with one ear or lug extending from each edge.

Inability to completely withdraw the cover plates is a further safety aspect of the inventive sharps disposal system, since this enables the attendant who is collecting the sharps in the collecting chamber to merely withdraw the two cover plates in order to collect the sharps, and then quickly push the cover plates back into closed position without having lost them from the tracks.

When the two cover plates have been pushed back into the closed position, the person making the collection depresses the spring trigger 84 in order to disengage the detent teeth 85 from the detent recess 63. This enables him to completely withdraw the entire collecting chamber 65 from the bottom of the holding chamber 21. It is to be noted that when this withdrawal is accomplished, the top cover plate 81 has been retained in the closed position, as shown in FIG. 1, in order to be assured that the sharps contained in the collecting chamber 65 cannot be accidentally spilled out of the collecting chamber. As soon as the collecting chamber 65 has been withdrawn from the bottom of the holding chamber 21, the articulated safety door 53 is pushed downwardly to the fully closed position and the spring biased lock 59 is projected above the surface of the front wall 34 to engage the yoke 56. At this point the bottom of the holding chamber is closed off by the bottom cover plate 61 and the articulated safety door 53 as shown in FIG. 7. The holding chamber 21 is now empty and ready to resume collection of more sharps.

The sharps disposal system which has been described will normally be made of a material which will enable it to be sterilized in an autoclave. Typically this material will be a metal such as aluminum or a stainless steel. Alternatively, the sharps disposal system may be formed of an autoclavable plastic such as rigid polyvinyl chloride, polycarbonate, polypropylene, or high density polyethylene. Other suitable materials will suggest themselves to the user.

It is to be noted that the foregoing description of the present invention shows that the collecting chamber 65 is inserted into the bottom of the holding chamber 21 along the center grooves on tracks 46 and 47 and along the bottom grooves or tracks 50 and 51 of the holding chamber. Those skilled in the art will recognize that using this double track means of attachment is not critical. The collecting chamber may be inserted into the bottom of the holding chamber by use of only the center tracks 46 and 47. Alternatively, the collecting chamber may be inserted into the bottom of the holding chamber by use of only the bottom tracks 50 and 51. If only the bottom tracks are used, it is within the scope of the present invention to eliminate the center tracks. However, the double track system is preferred from the point of safety, since it provides a more secure means of insertion.

In light of the foregoing disclosure, further alternative embodiments of the inventive sharps disposal system will undoubtedly suggest themselves to those skilled in the art. It is thus intended that the disclosure be taken as illustrative only, and that it not be construed in any limiting sense. Modifications and variations may be resorted to without departing from the spirit and the scope of this invention, and such modifications and variations are considered to be within the purview and the scope of the appended claims.

What is claimed is:

1. A container apparatus, suitable for use in a sharps disposal system, which comprises:
   a. a holding chamber, including a holding chamber body member having a rectangular cross-section with an open top and an open bottom, having front and back walls, and having right and left side walls;
   b. inwardly facing elongated first grooves on the inside of said right and left side walls, proximate the bottom of said holding chamber body member, and running from said back wall to said front wall;
   c. inwardly facing elongated second grooves on the inside of said right and left side walls, proximate the bottom of said holding chamber body member, positioned below said first grooves, and running from said back wall to said front wall;
   d. outwardly extending ribs located below and on the outside of the bottom edge of said right and left side walls, said ribs containing inwardly facing elongated third grooves proximate the bottom of the holding chamber body member and positioned below and outside of said first and second grooves, said ribs running from said back wall and extending upwardly along the corners formed by said holding chamber front wall with said side walls and continuing said inwardly facing third grooves vertically along said corners;
   e. a holding chamber bottom cover plate, slidably positioned in said first grooves to provide means to close the open bottom of said holding chamber body member, and to open said bottom by being withdrawn along said first grooves and under said holding chamber body member front wall; and,
   f. a safety door, slidably positioned in said third grooves and movable from a closed to an open position, said door in closed position enclosing said bottom cove plate below the holding chamber bottom and along the bottom of said holding chamber front wall to prevent the withdrawal of said bottom cover plate along said first grooves, and said safety door in open position being slidably movable within said third grooves from below said holding chamber bottom to a position along the outer surface of said holding chamber body member front wall above said first and second grooves, whereby said bottom cover plate may be withdrawn to open the holding chamber bottom.

2. A container apparatus according to claim 1 wherein said holding chamber includes a neck on the top of said chamber body member, and said neck has a lower portion and an upper portion with a closure plate movably positioned therebetween to be movable from a closed to an open position, thereby to allow articles to be dropped into said holding chamber.

3. A container apparatus according to claim 2 wherein said closure plate is pivotally mounted in said neck between said lower and upper portions with biasing means retaining said closure plate in closed position until external force is applied to pivot said closure plate to open position, whereupon said biasing means returns said closure plate to closed position when said external force is removed.

4. A container apparatus according to claim 2 wherein said upper neck portion has a circular cross-section said lower neck portion has a transitional cross-section changing from rectangular at said chamber body member to circular at said upper neck portion, and said closure plate has a circular configuration.

5. A container apparatus according to claim wherein said holding chamber includes locking means on the front wall of said holding chamber body member coacting with means on said safety door to retain said safety door in closed position enclosing said bottom cover plate, thereby preventing inadvertent premature opening of said safety door and withdrawal of said bottom cover plate to prematurely open the bottom of said holding chamber.

6. A container apparatus according to claim 5 wherein said locking means includes a spring biased lock projecting out of said front wall when in locked position to thereby retain said safety door in closed position, and said lock compressing said spring and seating within a recess in said front wall to thereby allow said safety door to be opened by sliding over said recessed lock to an open position along the outer surface of said front wall.

7. A container apparatus according to claim 6 wherein said coacting means on said safety door includes a yoke mating with said spring biased lock when said lock is projected out of said front wall.

8. A container apparatus according to claim 1 wherein said front wall is shorter than said back wall of said holding chamber body member and said chamber bottom slopes downwardly from the front wall to the back wall.

9. A container apparatus according to claim 8 wherein said chamber bottom slopes downwardly at an angle of about 30° from the horizontal.

10. A container apparatus according to claim 1 including a collecting chamber having a rectangular cross-section substantially congruent with the cross section of said holding chamber body member, having an open top and a closed bottom, having front and back walls, having right and left sidewalls, and further including inwardly extending ribs located above and on the inside of the top edge of said right and left collecting chamber side walls, said ribs running from said collecting chamber back wall to said collecting chamber front wall, said ribs containing inwardly facing elongated fourth grooves, and said ribs having dimensions enabling s id ribs to slidably fit within said second grooves of said holding chamber body member.

11. A container apparatus according to claim 10 wherein said inwardly extending ribs have an S-shaped cross-section.

12. A container apparatus according to claim 10 wherein a collecting chamber top cover plate is slidably positioned in said fourth grooves to provide means to close the open top of said collecting chamber and to open said top by being withdrawn along said fourth grooves and over said collecting chamber front wall.

13. A container apparatus according to claim 12 wherein said holding chamber bottom cover plate has a first detente element on its bottom surface, and said collecting chamber top cover plate has a second detente element on its top surface, and said first and second detente elements are dimensioned and positioned to releasably interlock said cover plates together when said collecting chamber is slid into said second grooves in said holding chamber, whereby said cover plates may be withdrawn in said first and fourth grooves as an interlocked unit to allow contents in said holding chamber to drop into said collecting chamber.

14. A container apparatus according to claim 13 wherein said first detente element is a recess on the bottom surface of said bottom cover plate, and said second detente element is a ribbon spring element having a first end attached to the leading portion of said top cover plate and a second free end including means mateable in said recess, whereby said ribbon spring may be gripped at the leading portion of said top cover plate to withdraw said cover plates as a unit.

15. A container apparatus according to claim 13 wherein said bottom cover plate includes means preventing said bottom cover plate from being totally withdrawn from said first grooves.

16. A container apparatus according to claim 13 wherein said top cover plate includes means preventing said top cover plate from being totally withdrawn from said fourth grooves.

17. A container apparatus according to claim 10 wherein said collecting chamber further includes outwardly extending ribs located on the outside of the top edge of said right and left collecting chamber side walls, said ribs running from said collecting chamber back wall to said collecting chamber front wall, and said ribs having dimensions enabling said ribs to slidably fit within said third grooves of said holding chamber body member.

18. A container apparatus according to claim 10 wherein said outwardly extending ribs of said holding chamber each contain a notch dimensioned to allow said outwardly extending ribs of said collecting chamber to slidably enter the third grooves of said holding chamber body member.

19. A container apparatus according to claim 18 wherein said notches are located in said outwardly extending ribs of the holding chamber in a transition segment of said ribs below and proximate the point where said ribs extend upwardly along said corners of the holding chamber front wall.

20. A container apparatus according to claim 1 wherein said safety door is flexible.

21. A container apparatus according to claim 20 wherein safety door is an articulated safety door.

22. A container apparatus according to claim 20 wherein said safety door comprises a flexible plastic planar structure.

23. Method of disposing of sharps from a medical environment which comprises the steps of:
  a. collecting sharps in a holding chamber having an open top and an open bottom, said open bottom having first grooves containing a bottom cover plate slidably in closed position, said open bottom containing second grooves below said first grooves, said open bottom containing third grooves below said first and second grooves, said third grooves extending upwardly along the vertical corners of the holding chamber front wall, and a locked flexible safety door slidably held in said third grooves at the holding chamber bottom and confining said bottom cover plate to prevent premature opening of the holding chamber bottom;
  b. unlocking the flexible safety door and sliding said safety door from the holding chamber bottom to the holding chamber front wall;
  c. inserting a collecting chamber into said second grooves of the holding chamber, said collecting chamber having a closed bottom and an open top, and said open top having fourth grooves containing a top cover plate slidably held in closed position; and said top cover plate having interlocking means mating with said holding chamber bottom cover plate;
  d. withdrawing said bottom and top cover plates along said first and fourth grooves, thereby opening said holding chamber bottom and said collecting chamber top, and thereby dropping accumulated sharps into said collecting chamber;
  e. returning said bottom and top cover plates along said first and fourth grooves to said closed position;
  f. withdrawing said collecting chamber from said second grooves of the holding chamber; and
  g. returning said safety door in said holding chamber third grooves to said closed position and locking said safety door to confine said bottom cover plate.

24. Method according to claim 23 wherein said bottom cover plate has a detent element at its bottom surface, said top cover plate has a detent element at its top surface, said detent elements interlock when said collecting chamber is inserted into said second grooves in step (c), said bottom and top cover plates are withdrawn as a unit in step (d), and said bottom and top cover plates are returned as a unit in step (e).

25. Method according to claim 23 wherein said open top of said holding chamber includes a closure plate held in closed position, said closure plate includes a gripping element, and force is applied on said gripping element to move said closure plate into open position when sharps are collected in said holding chamber.

26. Method according to claim 25 wherein said closure plate is pivotally mounted at said open top with a biasing spring holding said closure plate in closed position, force upon said gripping element moves said closure plate to open position, and release of said force allows said biasing spring to return said closure plate to closed position.

27. A container apparatus, suitable for use in a sharps disposal system, which comprises:
 a. a holding chamber, including a holding chamber body member having an open top and an open bottom, having front and back walls, and having front and left side walls;
 b. inwardly facing elongated first grooves on the inside of said right and left side walls, proximate the bottom of said holding chamber body member, and running from said back wall to said front wall;
 c. inwardly facing elongated second grooves on the inside of said right and left side walls, proximate the bottom of said holding chamber body member, positioned below said first grooves, and running from said back wall to said front wall;
 d. ribs located below the bottom edge of said right and left side walls, said ribs containing inwardly facing elongated third grooves proximate the bottom of the holding chamber body member and positioned below said first and second grooves, said ribs running from said back wall and extending upwardly along the corners formed by said holding chamber front wall with said side walls and continuing said inwardly facing third grooves vertically along said corners;
 e. a holding chamber bottom cover plate, slidably positioned in said first grooves to provide means to close the open bottom of said holding chamber body member, and to open said bottom by being withdrawn along said first grooves and under said holding chamber body member front wall; and,
 f. a safety door, slidably positioned in said third grooves and movable from a closed to an open position, said door in closed position enclosing said bottom cover plate below the holding chamber bottom and along the bottom of said holding chamber front wall to prevent the withdrawal of said bottom cover plate along said first grooves, and said safety door in open position being slidably movable within said third grooves from below said holding chamber bottom to a position along the outer surface of said holding chamber body member front wall above said first and second grooves, whereby said bottom cover plate may be withdrawn to open the holding chamber bottom.

28. A container apparatus according to claim 27 wherein said holding chamber includes a closure plate movably positioned at said open top to be movable from a closed to an open position, thereby to allow articles to be dropped into said holding chamber.

29. A container apparatus according to claim 28 wherein said closure plate is pivotally mounted at said open top with biasing means retaining said closure plate in closed position until external force is applied to pivot said closure plate to open position, whereupon said biasing means returns said closure plate to closed position when said external force is removed.

30. A container apparatus according to claim 27 wherein said holding chamber includes locking means on the front wall of said holding chamber body member coacting with means on said safety door to retain said safety door in closed position enclosing said bottom cover plate, thereby preventing inadvertent premature opening of said safety door and withdrawal of said bottom cover plate to prematurely open the bottom of said holding chamber.

31. A container apparatus according to claim 27 including a collecting chamber having a cross-section substantially congruent with the cross-section of said holding chamber body member, having an open top and a closed bottom, having front and back walls, having right and left sidewalls, and further including ribs located at the top edge of said right and left collecting chamber side walls, said ribs running from said collecting chamber back wall to said collecting chamber front wall, said ribs containing inwardly facing elongated fourth grooves, and said ribs having dimensions enabling said ribs to slidably fit within said second grooves of said holding chamber body member.

32. A container apparatus according to claim 31 wherein a collecting chamber top cover plate is slidably positioned in said fourth grooves to provide means to close the open top of said collecting chamber and to open said top by being withdrawn along said fourth grooves and over said collecting chamber front wall.

33. A container apparatus according to claim 32 wherein said holding chamber bottom cover plate has a first detente element on its bottom surface, and said collecting chamber top cover plate has a second detente element on its top surface, and said first and second detente elements are dimensioned and positioned to releasably interlock said cover plates together when said collecting chamber is slid into said second grooves in said holding chamber, whereby said cover plates may be withdrawn in said first and fourth grooves as an interlocked unit to allow contents in said holding chamber to drop into said collecting chamber.

34. A container apparatus according to claim 33 wherein said bottom cover plate includes means preventing said bottom cover plate from being totally withdrawn from said first grooves.

35. A container apparatus according to claim 33 wherein said top cover plate includes means preventing said top cover plate from being totally withdrawn from said fourth grooves.

36. A container apparatus according to claim 27 wherein said safety door is flexible.

* * * * *